United States Patent [19]

Nikolic

[11] Patent Number: 5,758,652
[45] Date of Patent: Jun. 2, 1998

[54] SYSTEM AND METHOD TO MEASURE THE CONDITION OF A PATIENTS HEART

[76] Inventor: Serjan D. Nikolic, 5026 Fulton St., San Francisco, Calif. 94121

[21] Appl. No.: 545,306

[22] Filed: Oct. 19, 1995

[51] Int. Cl.$^6$ ..................................................... A61B 5/02
[52] U.S. Cl. ..................................................... 128/673
[58] Field of Search ........................... 128/670, 672–675, 128/687, 690

[56] References Cited

U.S. PATENT DOCUMENTS

| | | |
|---|---|---|
| 3,962,697 | 6/1976 | Vreeland . |
| 4,347,851 | 9/1982 | Jundanian ........................ 128/672 |
| 4,404,974 | 9/1983 | Titus ................................ 128/670 |
| 4,556,063 | 12/1985 | Thompson et al. . |
| 4,712,562 | 12/1987 | Ohayon et al. .................. 128/672 |
| 4,798,211 | 1/1989 | Goor et al. ...................... 128/673 |
| 4,815,472 | 3/1989 | Wise et al. . |
| 4,884,576 | 12/1989 | Alt . |
| 4,899,752 | 2/1990 | Cohen ............................... 128/419 |
| 5,003,976 | 4/1991 | Alt .................................... 128/419 |
| 5,181,517 | 1/1993 | Hickey .............................. 128/673 |
| 5,199,438 | 4/1993 | Pearlman . |
| 5,222,020 | 6/1993 | Takeda . |
| 5,253,648 | 10/1993 | Walloch . |
| 5,337,750 | 8/1994 | Walloch ............................ 128/680 |
| 5,354,319 | 10/1994 | Wyborny et al. . |
| 5,368,040 | 11/1994 | Carney . |
| 5,387,259 | 2/1995 | Davidson . |
| 5,388,586 | 2/1995 | Lee et al. ......................... 128/704 |
| 5,390,679 | 2/1995 | Martin . |
| 5,391,190 | 2/1995 | Pederson et al. . |
| 5,402,794 | 4/1995 | Wahlstrand et al. . |
| 5,410,471 | 4/1995 | Alyfuku et al. . |
| 5,482,049 | 1/1996 | Addiss et al. .................... 128/673 |
| 5,535,752 | 7/1996 | Halperin et al. ................. 128/670 |
| 5,551,439 | 9/1996 | Hickey .............................. 128/673 |

FOREIGN PATENT DOCUMENTS

| | | |
|---|---|---|
| WO 88/01773 | 3/1988 | European Pat. Off. . |
| 3927-990 | 2/1991 | Germany ......................... 128/673 |
| 2013990C1 | 6/1994 | Russian Federation . |

OTHER PUBLICATIONS

"Pacing–Induced Dilated Cardiomyopathy Increases Left–to–Right Ventricular Systolic Interaction", David Farrar, Ph.D., et al., Ventricular Interaction with Cardiomyopathy, Ciculation, pp. 720–725, Mar. 3, 1993.

Fourth Edition Heart Disease, A Textbook of Cardiovascular Medicine, Part II, Normal & abnormal Circulatory Function, by Eugene Braunwald pp. 351–463.

Article entitled "Alterations in diastolic ventricular interdependence due to myocardial infartion," by William P. Santamore and louis Papa, Cardiovascular Research, May 30, 1988, pp. 726 and 731.

Article entitled "Effect of Right Ventricular Pressure on the End–Diastolic Left Ventricular Pressure–Volume Relationship before and after Chronic Right Ventricular Pressure Overload in Dogs without Pericardial", William C. Little et al, Circulation Research vol. 54, No. 6, Jun. 1984, pp. 719–730.

Article entitled "Dynamic biventricular interaction during systole", by William P. Santamore et al., Coronary Artery Disease, May/Jun. 1990, vol. 1 No. 3, pp. 298–305.

(List continued on next page.)

*Primary Examiner*—Jennifer Bahr
*Assistant Examiner*—Eric F. Winakur

[57] ABSTRACT

A system and method for measuring the heart condition of a patient is disclosed. The system includes a measuring device used to generate an absolute blood pressure signal indicative of the absolute blood pressure of the patient. A processing element receives and processes the absolute blood pressure signal, and generates (1) a filtered blood pressure signal by removing certain variations from the absolute blood pressure signal caused by respiratory activity of the patient; and (2) a set of parameters derived from the filtered blood pressure signal. The set of parameters measure certain aspects of the absolute blood pressure signal which are indicative of the performance and condition of the patient's heart.

47 Claims, 4 Drawing Sheets

OTHER PUBLICATIONS

Article entitled "Contractile function in canine right ventricle", by George D. Meier etal. The American Physiological Society, 1980, pp. H794–H7804.

Article entitled "Differentiation between systolic and diastolic dysfunction", by M. Federmann and O.M. Hess, European Heart Journal 1994, Supplement D, pp. 2–6.

Article entitled "Left ventricular unloading decreases relate of isovolumic right ventricular pressure decline", by Craig D. Brown et al. The American Physiological Society, 1993, pp. H1663–H1669.

Article entitled "Influence of Right Ventricular Filling Pressure on Left Ve Pressure and Dimension", by Charles E. Bemis et al., Mastolic Ventricular Interaction, Circulation Research, vol. XXXIV, Apr. 1974, pp. 498–504.

Article entitled "Influence of Left Ventricular Isovolumic Pressure Upon Right Ventricular Pressure Transients", by A.A. Oboler et al., Tufts University School of Medicine, Boston, Mass., Cardiology 58: 1973, pp. 32–44.

Article entitled "Reassessing Right Ventricular Function and Ventricular Interaction: The Role of Global Myocardial Contractile Mechanics", Michael K. Pasque, M.D., et al. The Science of Cardiac Surgery, Journal of Cardiac Surgery, vol. 1, No. 4, 1986, pp. 393–402.

Article entitled "Contribution of left ventricular contraction to the genration of right ventricular systolic pressure in the human heart", Michael P. Feneley et al. Pathophysiology and Natural History Ventricular Performance, Circulaion, vol. 71, No. 3, Mar. 1985, pp. 473–480.

Article entitled "Hemodynamic alterations during septal or right ventricular ischemia in dogs", David E. Fixler, M.D. et al., American Heart Journal, Feb. 1977, vol. 93, No. 2, pp. 210–215.

Article entitled "Right ventricular diastolic pressure–volume relations and regional dimensions during acute alterations in loading conditions", Louis J. Dell Italia, M.D. etal, Pathophysiology & Natural History–Ventricular Performance, Circulation vol. 77, No. 6, Jun. 1988, pp. 1276–1282.

Article entitled"Direct assessment of right ventricular transmural pressure" by William P. Santamore, PH.D. et al., Diagnostic Methods Pericardial Disease, Circulation, vol. 75, No. 4 Apr. 1987, pp. 744–747.

Article entitled "Significant left ventricular contribution to right ventricular systolic function", Ralph J. Damiano, Jr. et al. The American Physiological Society, 1991, pp. H1514–H1524.

Article entitled "Absence of right ventricular isovolumic relaxation in open–chest anesthetized dogs", Eivind S.P. Myhre et al., RV Isovolumic Relaxation Period, The American Physiological Society, 1992, pp. H1587–H1590.

Article entitled "Telemedicine: Remote Control Health Care", by Amy Roffmann, New Science and Technology, Ventricular Interaction With Cardiomyopathy, Circulation, Sep. 1995, Hemispheres, pp. 115–119.

Article entitled "Effects of left ventricular pressure reductions on right ventricular systolic performance", by Edna Chow et al., The American Physiological Society, 1989, pp. H1878–H1885.

Abstract entitled "Right Ventricular Systolic Dysfunction Limits Cardiac Output during Left Heart Bypass", James S. Tweddell, et al., Abstracts of the 62nd Scientific Sessions, Supplement II, Circulation, vol. 80, No. 4, Oct. 1989, pp. II–157.

Abstract entitled "Left Ventricular Afterload Parturbations and Right Ventricular Function: role of the Pericardium", Elvind SP Myhre et al., Abstracts of the 64nd Scientific Sessions, Supplement II, pp. II–671.

Abstract entitled "Mechanism of Systolic Ventricular Interaction", Hitoshi Yaku et al., Supplement II, Circulation, vol. 84, No. 4, Oct. 1991, pp. II–38.

SYSTEM AND METHOD TO MEASURE THE CONDITION OF A PATIENTS HEART

BACKGROUND OF THE INVENTION

1. Field of the Invention

The present invention relates to medical devices, and more particularly, to an apparatus and method for measuring an absolute blood pressure signal of a patient, generating a filtered blood pressure signal by substantially removing variations in the absolute blood pressure signal caused by the respiratory activity of the patient, and generating a set of parameters from the filtered blood pressure signal which can be evaluated to determine the condition of the patient's heart.

2. Description of the Related Art

The circulatory system in humans is responsible for transporting oxygen and other nutrients to the cells of the body. The circulatory system includes a heart, and a network or arteries, capillaries and veins. In a healthy patient the heart pumps blood with a certain pressure and volume to ensure that proper blood circulation in the body is maintained.

Referring to FIG. 1, a diagram of the human heart is illustrated. The heart 10 includes four chambers, including the right atria 12, the right ventricle 14, the left atria 16, and the left ventricle 18. The right atria 12 receives carbon dioxide laden blood returning from the body through the superior vena cava 20 and inferior vena cava 22. The right ventricle 14 receives blood from the right atria 12 through the triscuspid valve 24 located between the two chambers. The right ventricle 14 pumps blood through the pulmonary valve 26 and into the pulmonary artery 28 which carries the blood to the lungs. After receiving oxygen in the lungs, the blood is returned to the left atria 16 of the heart 10 through pulmonary veins 30. The blood in the left atria 16 passes through the mitral valve 32 and into the left ventricle 18. The blood in the left ventricle 18 is then pumped through the aortic valve 34, into the aorta 36, throughout the body via the network of arteries, capillaries, and finally returned to the heart 10 via the superior vena cava 20 and inferior vena cava 22.

Referring to FIG. 2, a graph of the continuous blood pressure in the right ventricle 14 during a heart cycle of a patient is shown. The graph 40 plots the pressure P in millimeters of mercury (mmHg) versus time during the heart cycle. The heart cycle is divided into (1) a systolic period and (2) a diastolic period. The systolic period includes the following phases: (a) isovolumic contraction; (b) ejection; and (c) isovolumic relaxation. The diastolic period includes the following: (d) a phase when the right ventricle 14 fills with blood; and (e) the end-diastolic point. The heart cycle shown in graph 40 begins with the end-diastolic phase of the previous cycle.

Congestive heart disease is a condition where the heart fails to adequately contract or relax during the heart cycle. As a consequence, systolic pressures in the heart are lower than normal and diastolic pressures are higher than normal. With the advancement of the disease, systolic pressure gradually decreases, and the diastolic pressure gradually increases. The improper blood pressure in the heart and circulatory system of the patient may cause a number of health problems for the patient. Patients with congestive heart disease are usually afflicted with a malady where congestion occurs in the lungs, liver and other organs of the body. Pulmonary edema, which is congestion in the lungs, is usually asymptomatic, and arises suddenly, without warning. The patient often does not know the edemic condition exists until it progresses to a near fatal state, and the patient suffers from a shortage of breath due to the congestion in the lungs. Edema is usually treated by admitting the patient into a hospital. The patient is then monitored and treated with medication until the congestion is substantially reduced or eliminated. Congestive heart disease is currently incurable. As the congestive condition of the patient progresses and the heart becomes weaker, bouts of edema tend to increase in intensity and frequency.

One problem of treating patients with congestive heart failure is that it is extremely costly. Each visit to the hospital may last several days and may cost tens of thousands of dollars. With its high degree of incidence, congestive heart disease is an extremely expensive health problem in the United States and other countries. The caring for patients with this disease represents a large percentage of the total expenditures for health care organizations, such as hospitals, health maintenance organizations, and represents a significant financial burden for health insurance companies and federal and local governments. The disease may also create a financial hardship for patients and their families.

In the medical field, it is known to implant a pressure sensor into the heart 10 of a patient. The pressure sensor is used to measure the absolute blood pressure in the heart for a number of health related reasons.

U.S. Pat. No. 5,368,040 entitled "*Apparatus and Method for Determining a Plurality of Hemodynamic Variables From a Single, Chronically Implanted Absolute Pressure Sensor*", issued to Carney on Nov. 29, 1994, discloses a blood pressure measuring technique. Carney uses a continuous absolute pressure measure in the right ventricle which generates a continuous pressure signal and a sense amplifier that receives ECG (R-waves and P-waves) signals from the heart. Carney teaches that the maximum systolic right ventricle pressure is equal to the maximum systolic pulmonary pressure. The maximum systolic right ventricle pressure and pulmonary artery pressure are therefore obtained by sampling the continuous pressure signal when the first derivative of the pressure signal equals zero (i.e., $d^1 \Delta P/\Delta t=0$) during ventricular systole. The maximum diastolic pulmonary artery pressure is obtained by sampling the continuous pressure signal when the second derivative equals zero (i.e., $d^2 \Delta P/\Delta t=0$) at the time of systole. Carney also teaches that the right atria systolic and diastolic pressure can be determined from the absolute blood pressure sensor in the right ventricle. Therefore, the atrial diastolic pressure is the same as the right ventricle pressure just prior to atrial contraction. Atrial systolic pressure is measured by sampling the continuous pressure signal when ($d^1 \Delta P/\Delta t =0$) after the start of atrial systole.

A number of problems are associated with the teachings of Carney. The first and second derivatives of an unfiltered absolute blood pressure signal is susceptible to inaccuracies because the first derivative and the second derivative of the continuous pressure signal tend to be very noisy. The use of the R-wave and the P-wave ECG signals are not necessary, and tend to complicate the circuitry required to perform the pressure measurements. Lastly, Carney provides no teaching or even a recognition that the systolic and diastolic pressures may be affected by the respiratory activity of the patient. The failure of Carney to consider the systolic and diastolic variations in pressure due to respiratory activity significantly reduces the usefulness of the Carney apparatus and method.

Systems are known where an absolute blood pressure signal, as measured by a transducer in the heart of a patient, is used to help control the rate of a pace maker in the patient. The absolute blood pressure signal is processed to recover information related to the respiratory activity of the patient. The respiratory and other information is then considered in controlling the rate of the pace maker. See for example U.S. Pat. No. 5,391,190 entitled "*Variation In Cardiac Chamber Volume or Pressure as a Controlling Parameter*" issued to Pederson on Feb. 21, 1995, and U.S. Pat. No. 4,884,576 entitled "*Self Adjusting Rate Responsive Cardiac Pacemaker and Method*" issued to Alt on Dec. 5, 1989.

It would therefore be desirable to have a system and method for measuring an absolute blood pressure signal of a patient, generating a filtered blood pressure signal by substantially removing variations in the absolute blood pressure signal caused by the respiratory activity of the patient, and generating a set of parameters from the filtered blood pressure signal which can be evaluated to determine the condition of the patient's heart.

SUMMARY OF THE INVENTION

The present invention relates to a system and method for measuring the heart condition of a patient. The system includes a measuring device used to generate an absolute blood pressure signal indicative of the absolute blood pressure of the patient. A processing element receives and processes the absolute blood pressure signal, and generates (1) a filtered blood pressure signal by substantially removing variations from the absolute blood pressure signal caused by respiratory activity of the patient and other artifacts of measurement; and (2) a set of parameters derived from the filtered blood pressure signal. The set of parameters measure certain aspects of the filtered blood pressure signal which are indicative of the performance and condition of the patient's heart.

The system also includes a communication element and a processing station. The communication element transmits the filtered blood pressure signal and the set of parameters to the processing station. The processing station then processes this information, and presents it to medical personnel in a user friendly format. The medical personnel can then conveniently and accurately evaluate the condition of the patient, and subscribe a medical treatment for the patient based on the transmitted information. In one embodiment, the patient and the processing station are located at different locations. The communication element is capable of transmitting the filtered blood pressure signal and the set of parameters received from the patient to a remote location where the processing station is located, such as in a hospital or a doctor's office. A doctor can thus measure a patient from the remote location, diagnose congestive heart related problems, such as edema, and subscribe a treatment to correct the condition. With early detection, the condition can be treated sooner than previously possible, and most likely without admitting the patient to the hospital. The predicament of the patient is therefore improved, and many of the costs associated with admitting the patient into a hospital are eliminated.

The present invention provides numerous advantages. The filtering technique and the set of parameters used to measure the heart performance and condition of a patient provide medical personnel with a wealth of information to accurately measure, diagnose and treat patients with congestive heart disease. The present invention provides an efficient, highly accurate and realistic portrayal of the actual heart condition of the patient, never before possible with prior art medical instrumentation or techniques.

DESCRIPTION OF THE DRAWINGS

The features and advantages of the present invention will be apparent from the following description in which.

DESCRIPTION OF THE PREFERRED EMBODIMENT

Figure 1:
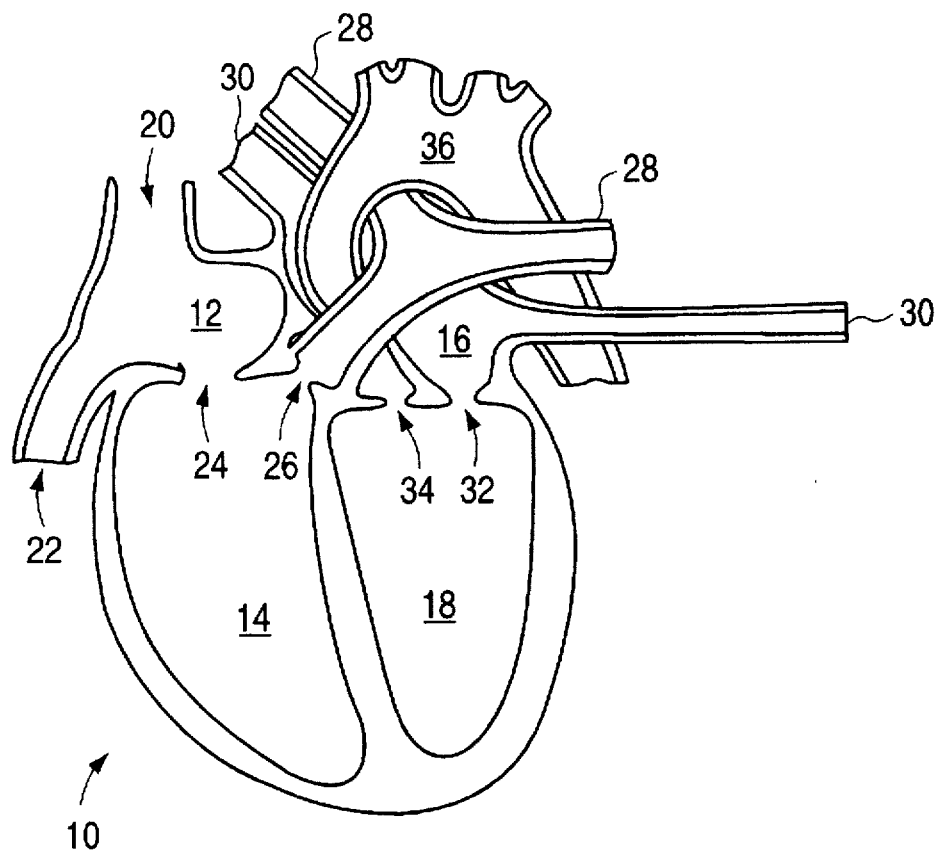
FIG. 1 illustrates a heart of a human patient.
Figure 2:
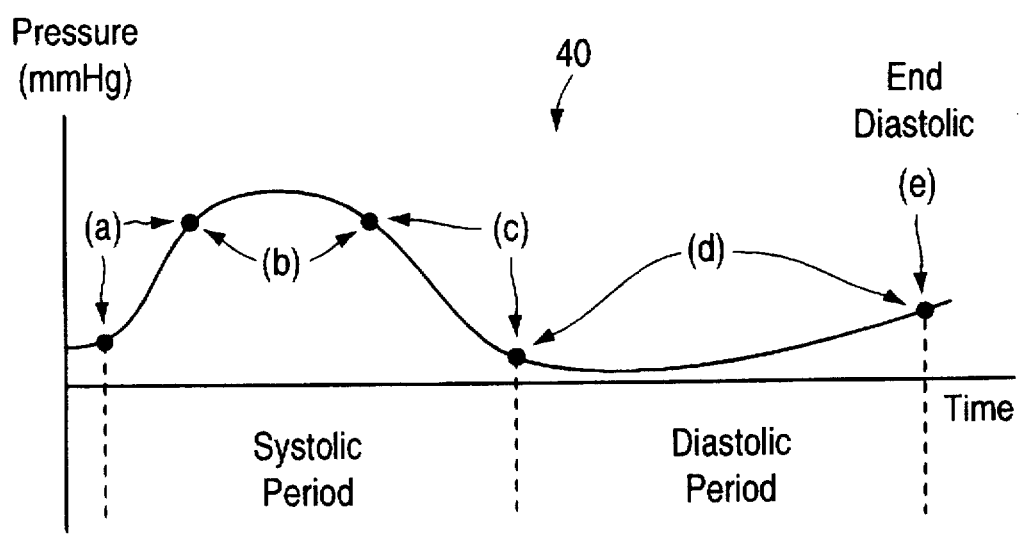
FIG. 2 illustrates a continuous blood pressure signal measured in the right ventricle of a patient.
Figure 3:
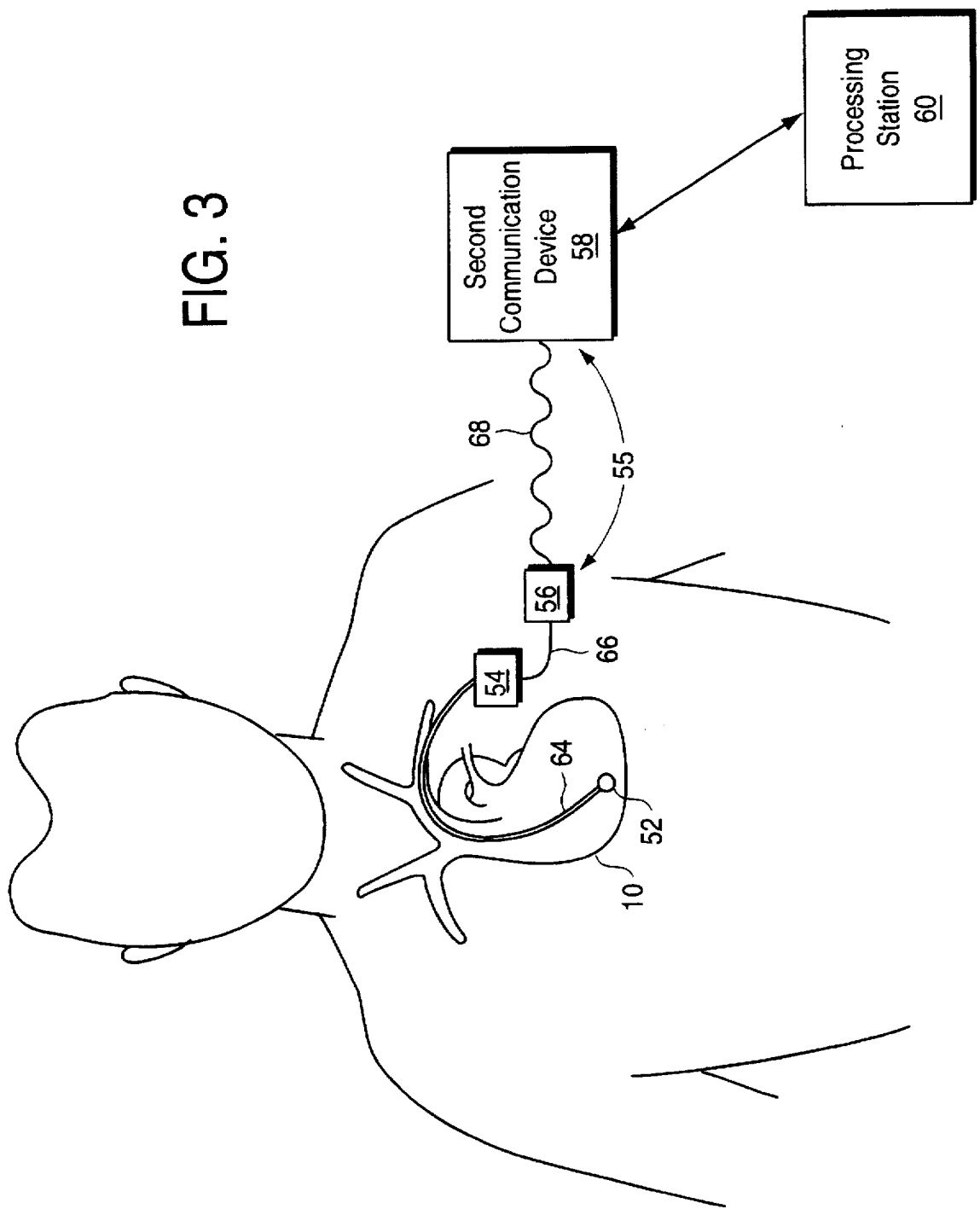
FIG. 3 illustrates a system for measuring the blood pressure in a patient according to the present invention.

Referring to FIG. 3, a system to measure the heart condition of a patient according to the present invention is shown. The system 50 includes a blood pressure sensor 52, a processing element 54, a communication element 55, including a first communication device 56, a second communication device 58, and a processing station 60. A first interconnect 64 couples the blood pressure sensor 52 and the processing element 54. A second interconnect 66 couples the processing element 54 and the first communication device 56. A link 68 couples the first and second communication devices 56 and 58 through the skin of the patient. The blood pressure sensor 52, the processing element 54, and the first communication device 56 are preferably chronically implanted into the body of the patient. The link 68 between the first communication 56 device and the second communication device 58 is preferably wireless. In one embodiment, the Conifix model number 501112 from the InnoMedica Corporation, Mineappolis Minn., is used for the interconnect 64 and the interconnect 66.

The blood pressure sensor 52 is implanted in the right ventricle 14 of the heart 10. The blood pressure sensor 52 measures and generates a continuous signal indicative of the absolute blood pressure in the right ventricle 14. The absolute blood pressure is measured relative to a vacuum or zero pressure. In one embodiment, the pressure sensor 52 can be any type of solid state blood pressure transducer, such as model number SPC-320 from the Millar Corporation, Houston, Tex. Such a blood pressure sensor 52 is preferably implanted using a catheter or some other technique. In alternative embedments, the absolute blood pressure can be measured using a number of other techniques, such as by using ultrasound, Doppler, a cuff or some other measuring technique.

The processing element 54 is an electronic component designed to be implanted under the skin of the patient. The processing element 54 processes the absolute blood pressure signal, and generates a filtered blood pressure signal in response. The processing element 54 also analyses the filtered blood pressure signal, and generates a set of parameters indicative of the heart condition of the patient. Each of the parameters measure a particular aspect of the patient's heart cycle which may be used by a doctor to determine the systolic and diastolic function of the heart. In accordance with various embodiments of the present invention, the processing element 54 may include either digital circuitry, analog circuitry, or a combination thereof.

The first communication device 56 and the second communication device 58 of the communication element 55 are designed to communicate through the skin of the patient. The purpose of the first communication device 56 is to transmit the filtered blood pressure signal and the set of parameters generated by the processing element 54 external to the body of the patient. The purpose of the second communication device 58 is to transmit control information to the first communication device 56, which in turn controls the processing element 54. Such information may include "power up" and "power down" signals, signals to instruct the processing element 54 to generate a filtered blood pressure signal and a corresponding set of parameters, timing signals to instruct the processing element 54 to generate the same at a specific time, or at specific intervals of time, test or calibration signals, and other control related information. The second communication device 58 is also used to temporarily store filtered blood pressure signals and their corresponding set of parameters received from the first communication device 56. The second communication device stores this information until it is transmitted to the processing station 60. The second communication device can also be used to receive information from the processing station 60, and to up-load this information to the processing element 54 via the first communication device 56. This feature permits new functionally and processing capabilities to be added to the processing element 54 after it has been implanted into the body of the patient.

A number of communication mediums may be used to establish the link 68 between the first communication device 56 and the second communication device 58. The link 68 may be radio waves. See the transdermal telemetry system that is described in the above-mentioned U.S. Pat. No. 5,368,040 issued to Carney, and incorporated by reference herein. The link 68 may rely on light waves or pulses. See U.S. Pat. No. 5,387,259, entitled "*Optical Trainsdermal Linking Method for Transmitting Power and a First Power Stream While Receiving a Second Data Stream*", issued on Feb. 7, 1995 to Davidson, and incorporated by reference herein. The link 68 can also be a hard-wired port implanted through the skin of the patient. With this embodiment, the second communication device 58 may be "plugged" into the port when communication between the first communication device 56 and second communication device 58 is desired. The link 68 can also be acoustic. With this embodiment, both the first communication device 56 and the second communication device 58 are capable of transmitting, receiving and decoding acoustic audio signals through the skin of the patient.

In accordance with various embodiments of the invention, the processing station 60 may be located in a number of different places. In one embodiment, the processor station 60 may be located in close proximity to the patient, such as in the home of the patient, or in a nursing home where the patient is residing. In another embodiment, the processing station 60 may be located in a remote location relative to the patient. For example, the patient is located at home, and the processing station 60 is located in a hospital or doctor's office. The patient is then required to either (1) visit the hospital or a doctor's office to directly down-load filtered blood pressure signals and related sets of parameters to the processing station 60; or (2) an assistant can bring the second communication device 58 storing such information to the processing station 60. In yet another embodiment, the second communication device 58 has the ability to transmit filtered blood pressure signals and the corresponding sets of parameters to the processor station 60 from a remote location. For example, the second communication device 58 may contain a modem for transmitting the stored information to the remote processing station 60 by way of the telephone lines. In another example, the second communication device 58 may be a home computer that is capable of transmitting the filtered blood pressure signals and related parameters to the processing station 60 via the Internet, or some other computer network. In yet another example, the second communication device 58 is a radio transmitter/receiver that is capable of transmitting and receiving information to and from the processing station 60 using a wireless communication protocol. Regardless of the transmission medium, these embodiments all have the advantage of permitting the patient to be monitored by a doctor from a remote location, without requiring the patient to visit the doctor's office or be admitted into the hospital.

The processing station 60 is a computer, such as a personal computer, work station, mini-computer or a main frame. The processing station 60 is programmed to perform data processing on the information received from the patient. For example, the processing station 60 is programmed to create a specific record for each patient. Each record may include previously measured filtered blood pressure signals, their corresponding set of parameters, and other medical information related to the patient. The processing station 60 is also programmed to present the filtered blood pressure signals and parameters in a user friendly format. A doctor may direct the processing station 60 to compile and display a number of current and previous filtered blood pressure signals and their corresponding set of parameters, sampled over a period of time. The compiled information can then be used to interpret certain trends in the patient's heart condition over time. For example, a plot illustrating a steady drop in a patients maximum systolic pressure over a defined period of time may indicate a weakening of the patient's heart. A doctor can then prescribe a medical treatment to correct the problem, before the patient progresses into a more severe condition requiring admission into a hospital. In summary, the processing station 60 may perform any type of data processing on the received information that may help medical personal monitor, diagnose and treat a congestive heart condition of a patient.

The absolute blood pressure in the right ventricle 14 is affected by the respiratory activity of the patient. The normal increase and decrease of pressure in the chest and lungs, caused by breathing, typically causes a corresponding increase or decrease of blood pressure in the heart. Therefore, analyzing an absolute blood pressure signal may lead to an incorrect diagnosis because it is difficult to determine if pressure changes are due to problems related to congestive heart disease, or the normal respiratory activity of the patient. The Applicant has therefore devised a way to filter and substantially remove variations in the absolute blood pressure signal caused by the respiratory activity of the patient.

Figure 4:
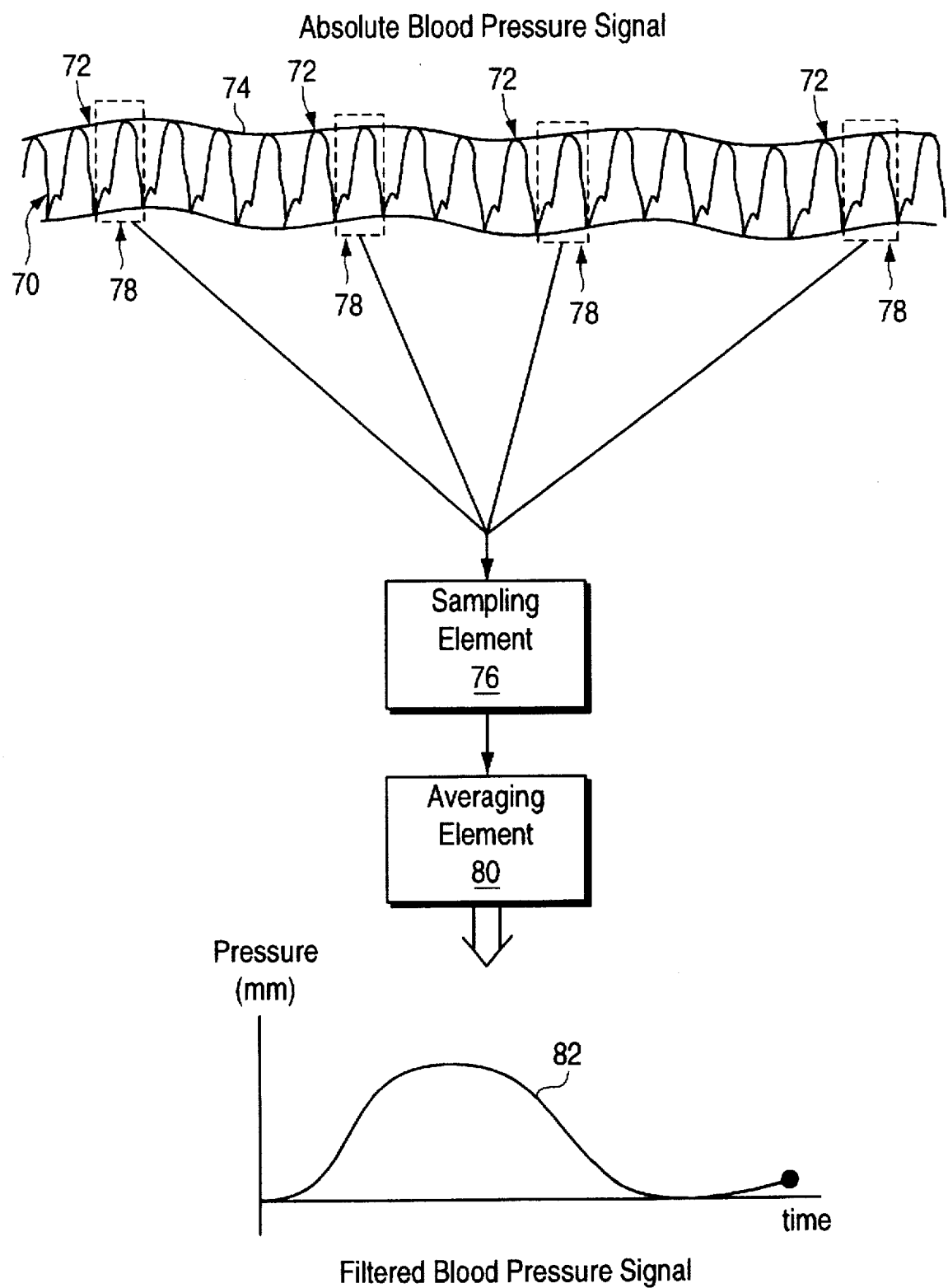
FIG. 4 illustrates the steps of generating a filtered blood pressure signal from an absolute blood pressure signal according to the present invention.

Referring to FIG. 4, an illustration of the steps required to generate a filtered blood pressure signal from an absolute blood pressure signal according to the present invention is shown. The figure illustrates a continuous absolute blood pressure signal 70 including a series of heart cycles as generated by the blood pressure sensor 52. The absolute blood pressure signal 70 is characterized by a number of peaks 72 and valleys 74 caused by the respiratory cycles of the patient. A sampling element 76, contained in the processing element 54, samples a selected heart cycles 78 during each of the respiratory cycles. The samples are preferably taken at the same phase in each respiratory cycle. The sampled heart cycles 78 are then provided to an averaging element 80, also contained in the processing element 54. The averaging element 80 averages the sampled heart cycles 78, and generates a filtered blood pressure signal 82. It should be noted that the number of sampled heart cycles 78 per respiratory cycle, the phase of the sampled heart cycles 78 in the respiratory cycle, and the number of respiratory cycles sampled, are all design choices. The Applicant recommends that one heart cycle sample at the peak exhalation period, or the peak inhalation period, of three or four consecutive respiratory cycles be used to generate the filtered blood pressure signal 82.

A number of benefits are realized by generating the filtered blood pressure signal 82. Most significantly, the filtering of the absolute blood pressure signal 70 removes most of the variants caused by the respiratory activity of the patient and other artifacts of measurement. The filtered blood pressure signal 82 therefore offers a more accurate indicator of the performance and condition of the patient's heart. The filtered blood pressure signal is also analyzed using a predefined set of parameters. Each one of the set of parameters is indicative of the ability and efficiency of the patient's heart, and quality of the patient's heart cycle. These parameters provide an efficient, highly accurate and realistic measurement of the actual heart condition of the patient.

Figure 5:
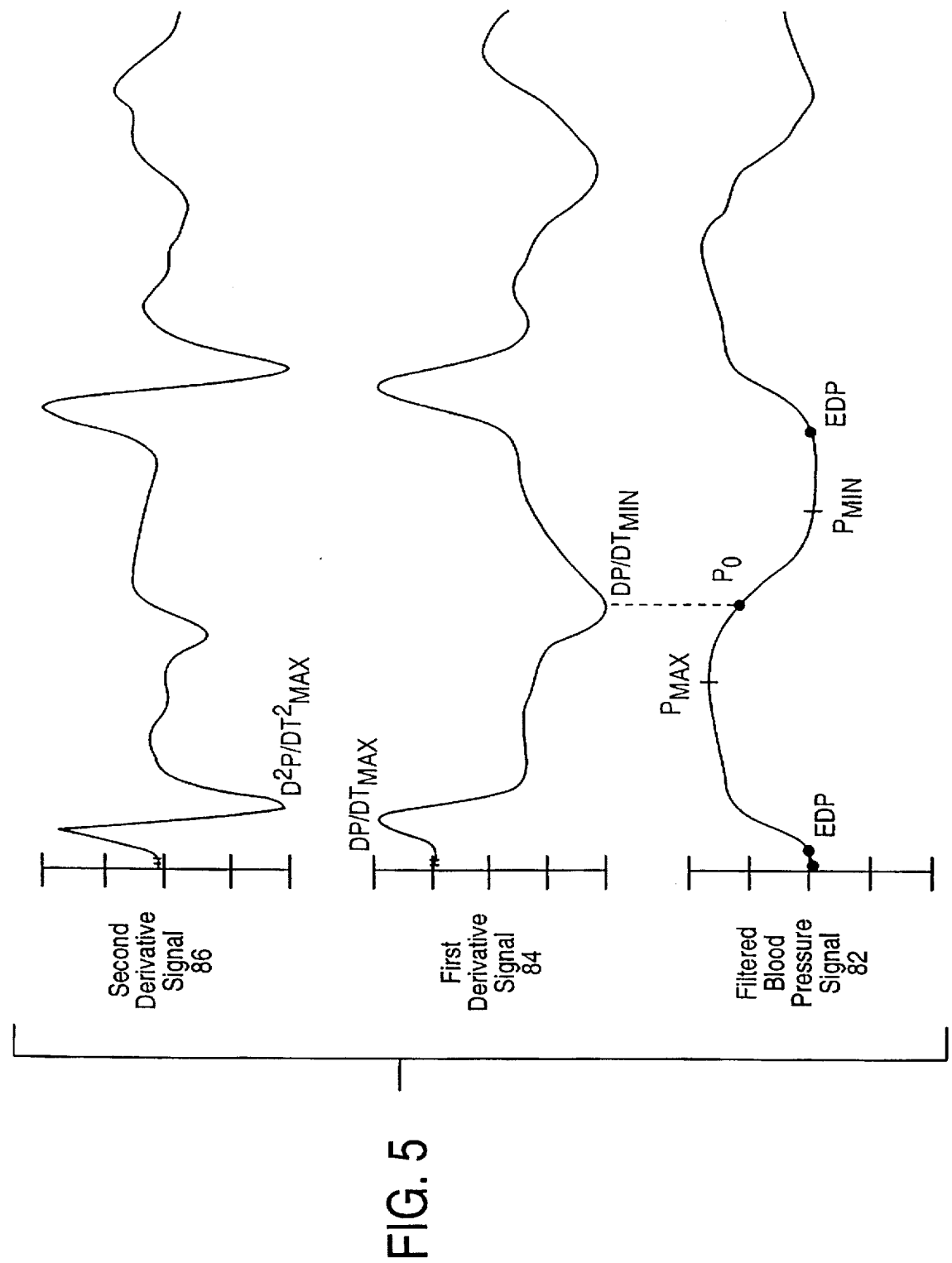
FIG. 5 illustrates the measured parameters from the filtered blood pressure signal, a first derivative signal, and a second derivative signal of the filtered blood pressure signal in accordance with the present invention.

Referring to FIG. 5, a plot illustrating the filtered blood signal 82, a first derivative signal 84, and a second derivative 86 of the filtered blood pressure signal 82 is shown. The set of parameters are derived from the filtered blood pressure signal 82; the first derivative signal 84 and the second derivative signal 86. Each of the set of parameters are calculated in the processing element 54 after the filtered blood pressure signal has been generated.

In one embodiment, the processor element 54 includes an analog-to-digital (A/D) converter to sample and digitize the absolute blood pressure signal 70, and a microcontroller to filter the absolute blood pressure signal and to generate the set of parameters, and a read only memory (ROM) for storing the microcode used to control the microcontroller. One type of microcontroller that can be used with the present invention is the PIC 16C7X made by the Microchip Corporation, Chandler, AZ. The microcontroller generates the filtered blood pressure signal 82 by storing the sampled and digitized absolute blood pressure signal from the A/D converter over a period of three or more respiratory cycles. A heart cycle 78 at the same phase of each of the three or more respiratory cycles is then selected, for example at either the peak inhalation phase or the peak exhalation phase. A base heart cycle is then selected among one of the sampled heart cycles 78. The sampled heart cycles are then interpolated to match the wave form time scale of the base heart cycle so that all sampled heart cycles have the same number of time divisions. The endpoints of the sampled heart cycles 78 are also interpolated since it is unlikely that the sampled heart cycles will all begin and end at the same pressures due to the granularity of the sampling in time. The selected heart cycles 78 are then averaged pointwise with the base heart cycle. Once the filtered blood pressure signal 82 is derived, the microcontroller performs an (n) point differential least-squares fit convolution on the filtered blood pressure signal 82 to obtain the first derivative signal 84, and then repeats this process on the first derivative signal 84 to obtain the second derivative signal 86. The microcontroller then calculates the set of parameters from the equations provided below. In another alternative embodiment, an analog computer may be used to filter the absolute blood pressure signal to generate the set of parameters.

The set of parameters include the following measurements:

(1) dP/dtMAX—This parameter is a measure of the maximum pressure time derivative derived from the signal 84. It is an indicator of the peak pressure increase in the right ventricle 14 during isovolumic contraction. This parameter is related to the contractile ability of the right ventricle 14. The larger the amplitude of dP/dtMAX, the better the heart contraction.

(2) Normalized dP/dtMAX (NdP/dtMAX)—NdP/dtMAX is a useful index of systolic function because it is less dependent on the absolute pressure measurement in the right ventricle 14. This parameter has the same meaning as dP/dtMAX. The larger the amplitude of NdP/dtMAX, the better the heart condition.

(3) Time to dP/dtMAX$_t$—This parameter is a measure of the time to dP/dtMAX. This parameter is related to the contractile properties of the right ventricle 14. The shorter the time to dP/dtMAX$_t$, the better the systolic function. This parameter is not sensitive to absolute pressure, but it is sensitive to the heart rate. Therefore, this parameter is also provided in a normalized form.

(4) Normalized time to dP/dtMAX$_t$ (NdP/dtMAX$_t$)—This parameter is normalized to the heart rate in accordance with the equation NdP/dtMAX$_t$=(120/HR −0.49).

(5) $d^2$P/dtMIN—This parameter is a measure of the first minimum of the second derivative signal 86.

(6) $d^2$P/dtMIN @ (5%)—This parameter is a measure of the pressure at (5%) of $d^2$P/dtMIN at the down slope of the second derivative.

(7) PMAX—This parameter is a measure of the peak systolic ventricular pressure derived from signal 82. The peak pressure is a measure of the ability of the right ventricle 14 to generate blood pressure. It is a useful indicator of the overall hemodynamic status of the patient.

(8) dP/dtMIN—This parameter is a measure of the minimum of the first derivative signal 84. It represents the peak rate of pressure decrease during isovolumic relaxation.

(9) dP/dtMIN$_t$—This parameter is a measure of the time to dP/dtMIN. It is a measure of the relaxation properties of the right ventricle 14.

(10) Systolic Time—This parameter measures the difference between (dP/dtMIN$_t$–dP/dtPMAX$_t$).

(11) PMIN—This parameter is a measure of the minimum ventricular pressure taken from the filtered signal 82. It is a useful indicator of the ability of the right ventricle 14 to relax.

(12) PO—This parameter is a measure of the pressure at the time of dP/dtMIN.

(13) Time constant of isovolumic pressure decay tau ($\tau$). The constant of isovolumic pressure decay ($\tau$) is calculated by using a least squares fit or some other mathematical relaxation algorithm for a number (m) of points $P_1$ through $P_m$ sampled during the iso-relaxation phase of the filtered blood pressure signal 82. In accordance with the least squares fit algorithm, the heart relaxation time constant ($\tau$) is derived by systematically varying the coefficients (A) and (B) in the equation P=Ae$^{-t/\tau}$+B for each sampled pressure point $P_1$ through $P_m$ to achieve an optimal fit for the sampled data points. This parameter is indicative of the process of relaxation.

(14) PINF—This parameter is a measure of the asymptote of the isovolumic relaxation pressure exponential. This asymptote allows the estimate of completeness of relaxation. Tau and and PINF are determined from the exponential fit of the form $P=(PO-PINF)e^{(-t/\tau)}+PINF$. In accordance with the least squares fit algorithm, the tau ($\tau$) and PINF are determined with the best fit of the sampling points between PO and PMIN + the pressure at a predetermined number of sample points prior to PMIN. In one embodiment, the predetermined number is ten.

(15) MDP—The mean diastolic pressure measurement is calculated by sampling a number (n) of pressure points $P_1$, $P_2$, through $P_n$ during the diastolic period of the filtered blood pressure signal 82. The mean diastolic pressure (MDP) measurement is then calculated from equation ($MDP=P_1+P_2+ \ldots P_n/n$).

(16) EDP—This parameter is a measure of the pressure of the filtered blood pressure signal 82 at a time corresponding to a predetermined percentage of dP/dtMAX on the upstroke of dP/dt. In one embodiment, the predetermined percentage is (5%). The end diastolic pressure indicates passive elastic properties of the ventricle. Combined with the constant of isovolumic pressure decay ($\tau$) and PINF, this parameter can provide an insight into the changes in the active process of relaxation and passive elastic properties of the right ventricle 14.

(17) $EDP_r$—This parameter is a measure of the time to end diastolic pressure.

(18) Diastolic Time—This parameter measures the difference between ($EDP_r$-dP/dt$MIN_r$).

(19) Heart Rate (HR)—This parameter is determined by 60/$EDP_r$.

The above parameters provide a highly accurate representation of the condition and quality of the heart of a patient. With proper use, a doctor can accurately measure the condition of a patient's heart. For example, a patient can be directed to sample and generate a set of parameters at specified time intervals subscribed by a doctor. This information can then be transmitted to the doctor and analyzed at a remote location. By comparing the relative differences of a current set of parameters with previous sets of parameters, the condition of the patient's heart can be ascertained.

While the present invention has been described in relationship to the embodiments described in the accompanying specification, other alternatives, embodiments and modifications will be apparent to one skilled in the art. For example, the blood pressure sensor 52 can be located in any one of the chambers of the heart, the lungs, an artery or vein, or any other location in the circulatory system. In another embodiments, a non-evasive technique to measure blood pressure the blood pressure of a patient, such as the use of any medical instrumentation used to measure blood pressure external to the body may be used. In such alternative embodiments, the use of internal processing and communication devices may not be needed. In yet another alternative embodiment, the blood pressure sensor 52 and the processing element 54 can be integrated into a single unit that is implanted into the heart of the patient. In yet another embodiment, the internal communication device can be coupled directly to the pressure sensor. The internal communication device would receive and transmit the absolute blood pressure signal external to the body of the patient, using for example RF signals. The absolute blood pressure signal would then be processed by a processing element, external to the body of the patient. The present invention can also be used to measure the performance of the heart in heart transplant patients, and with patients with faulty valves and the like. It is intended that the specification be only exemplary, and that the true scope and spirit of the invention be indicated by the following claims.

What is claimed is:

1. A system used to measure the heart condition of a patient, the system comprising:

a measuring device configured to measure absolute blood pressure of the patient and to generate an absolute blood pressure signal indicative of the absolute blood pressure of the patient during a plurality of respiratory cycles of the patient; and a processing element to process the absolute blood pressure signal, the processing element for generating a filtered blood pressure signal from the absolute blood pressure signal by substantially removing variations from the absolute blood pressure signal caused by respiratory activity of the patient during the plurality of respiratory cycles, the processing element further including a sampling element to sample the absolute blood pressure signal during a plurality of selected heart cycles that occur during the plurality of respiratory cycles and to generate a plurality of sampled blood pressure signals, and an averaging element to generate the filtered blood pressure signal by averaging the plurality of sampled blood pressure signals.

2. The system of claim 1, wherein the selected heart cycles occur at a selected phase of each of the plurality of respiratory cycles.

3. The system of claim 2, wherein the selected phase is an end exhalation phase of each of the plurality of respiratory cycles.

4. The system of claim 2, wherein the selected phase is an end inhalation phase of each of the plurality of respiratory cycles.

5. The system of claim 1, wherein the processing element further generates a derivative signal of the filtered blood pressure signal by performing a mathematical derivative on the filtered blood pressure signal.

6. The system of claim 1, wherein the processing element is further configured to derive one parameter from the filtered blood pressure signal that is indicative of the condition of the heart of the patient.

7. The system of claim 6, wherein the one parameter is a peak systolic pressure measurement of the filtered blood pressure signal.

8. The system of claim 6, wherein the one parameter is a minimum diastolic pressure measurement of the filtered blood pressure signal.

9. The system of claim 6, wherein the one parameter is a mean diastolic pressure measurement of the filtered blood pressure signal.

10. The system of claim 6, wherein the one parameter is a time constant of isovolumic pressure decay indicative of the rate at which the heart of the patient relaxes.

11. The system of claim 6, wherein the one parameter is a contraction signal indicative of the ability of the heart of the patient to contract.

12. The system of claim 11, wherein the processing element is configured to generate the contraction signal by determining a change in blood pressure over time during an isovolumic contraction phase of the filtered blood pressure signal.

13. The system of claim 11, wherein the contraction signal includes one of the following group of measurements derived from the filtered blood pressure signal, the group including the measurements of (a) a maximum pressure time derivative; (b) a normalized maximum pressure time derivative; (c) a time to the maximum pressure time derivative; and (e) a normalized time to the maximum pressure time derivative.

14. The system of claim 6, wherein the one parameter is a relaxation signal indicative of the ability of the heart of the patient to relax.

15. The system of claim 14, wherein the processing element generates the relaxation signal by calculating a change in pressure over time during an isovolumic relaxation phase of the filtered blood pressure signal.

16. The system of claim 14, wherein the relaxation signal includes one of the following group of measurements which are derived from the filtered blood pressure signal, the group including the measurements of (a) a minimum pressure time derivative; (b) a time to the minimum pressure time derivative;

(c) the value of the filtered blood pressure signal at the time to the minimum pressure time derivative; (d) a minimum value of the second derivative; and (e) the blood pressure at a predetermined point in the down slope of the second derivative of the filtered blood signal.

17. The system of claim 6, wherein the one parameter includes at least one of the following measurements: (a) end diastolic pressure; and (b) a time to the end diastolic pressure.

18. The system of claim 6, wherein the one parameter is a time measurement of a diastolic period of the filtered blood pressure signal.

19. The system of claim 6, wherein the one parameter is a measure of an asymptote of isovolumic relaxation pressure exponential derived from the filtered blood pressure signal.

20. The system of claim 6, wherein the one parameter is a measure of the heart rate of the patient.

21. The system of claim 1, wherein the processing element is an implantable device designed to be implanted into the body of the patient and includes digital circuitry configured to process the absolute blood pressure signal and to generate the filtered blood pressure signal by removing certain variations from the absolute blood pressure signal due to respiratory activity of the patient during the plurality of respiratory cycles.

22. The system of claim 1, wherein the processing element is an implantable device designed to be surgically implanted into the body of the patient and includes analog circuitry configured to process the absolute blood pressure signal and to generate the filtered blood pressure signal by removing certain variations from the absolute blood pressure signal due to respiratory activity of the patient during the plurality of respiratory cycles.

23. The system of claim 1, wherein the measuring device is configured to be implanted in a chamber of the patient's heart and is configured to measure the absolute blood pressure flowing through the chamber of the patient's heart.

24. The system of claim 1, wherein the measuring device and the processing unit are integrated into a housing.

25. The system of claim 24, wherein the housing is intended to be implanted into the heart of the patient.

26. A method to analyze the heart condition of a patient, comprising the steps of:
measuring absolute blood pressure of the patient during a plurality of respiratory cycles of the patient;
generating an absolute blood pressure signal indicative of the absolute blood pressure of the patient during the plurality of respiratory cycles of the patient;
generating a filtered blood pressure signal from the absolute blood pressure signal by substantially removing variations from the absolute blood pressure signal caused by respiratory activity of the patient during the plurality of respiratory cycles;
the step of generating the filtered blood pressure signal further including the steps of:
sampling the absolute blood pressure signal during each of a plurality of selected heart cycles that occur over course of the plurality of respiratory cycles;
generating sampled blood pressure signals;
averaging the sampled blood pressure signals;
generating the filtered blood pressure signal from the averaged sampled blood pressure signals; and
analyzing the condition of the patient's heart based on the filtered blood pressure signal.

27. The method of claim 26, wherein the sampling step occurs at the same phase of each of the plurality of respiratory cycles.

28. The method of claim 27, wherein the sampling step occurs at an end exhalation phase of each of the plurality of respiratory cycles.

29. The method of claim 27, wherein the sampling step occurs at an end inhalation phase of each of the plurality of respiratory cycles.

30. The method of claim 26, wherein the processing step further comprises the step of generating a derivative signal of the filtered blood pressure signal by performing a mathematical derivative on the filtered blood pressure signal.

31. The method of claim 25, wherein the processing step further comprises the step of deriving one parameter from the filtered blood pressure signal that is indicative of the condition of the heart of the patient.

32. The method of claim 31, wherein the step of deriving the one parameter comprises the step of deriving a peak systolic pressure measurement of the filtered blood pressure signal.

33. The method of claim 31, wherein the step of deriving the one parameter comprises the step of deriving a minimum diastolic pressure measurement of the filtered blood pressure signal.

34. The method of claim 31, wherein the step of deriving the one parameter comprises the step of deriving a mean diastolic pressure measurement of the filtered blood pressure signal.

35. The method of claim 31, wherein the step of deriving the one parameter comprises the step of deriving a time constant of isovolumic pressure decay indicative of the rate at which the heart of the patient relaxes.

36. The method of claim 31, wherein the step of deriving the one parameter comprises the step of deriving a contraction signal indicative of the ability of the heart of the patient to contract.

37. The method of claim 36, wherein the step of generating the contraction signal further includes the step of measuring a change in blood pressure over time during an isovolumic contraction phase of the filtered blood pressure signal.

38. The method of claim 36, further comprising the step of generating at least one of the following measurements after the step of deriving the contraction signal, measurements including (a) a maximum pressure time derivative; (b) a normalized maximum pressure time derivative; (c) a time to the maximum pressure time derivative; and (e) a normalized time to the maximum pressure time derivative.

39. The method of claim 31, wherein the step of deriving one parameter comprises the step of deriving a relaxation signal indicative of the ability of the heart of the patient to relax.

40. The method of claim 31, wherein the step of generating the relaxation signal further includes the step of calculating a change in pressure over time during an isovolumic relaxation phase of the filtered blood pressure signal.

41. The method of claim 40, wherein the step of generating the relaxation signal includes at least one of the following steps of generating (a) a minimum pressure time derivative; (b) a time to the minimum pressure time derivative; (c) the value of the filtered blood pressure signal at the time to the minimum pressure time derivative; (d) a minimum value of the second derivative; and (e) the blood pressure at a predetermined point in the down slope of the second derivative of the filtered blood signal.

42. The method of claim 31, wherein the step of generating the one parameter includes the step of generating at least one of the following measurements: (a) end diastolic pressure; and (b) a time to the end diastolic pressure.

43. The method of claim 31, wherein the step of generating the one parameter includes the step of generating a time measurement of a diastolic period of the filtered blood pressure signal.

44. The method of claim 31, wherein the step of generating the one parameter further includes the step of generating a measure of an asymptote of isovolumic relaxation pressure exponential derived from the filtered blood pressure signal.

45. The method of claim 31, wherein the step of generating the one parameter further includes the step of generating a signal indicative of a measure of the heart rate of the patient.

46. The method of claim 25, further comprising the step of subscribing a medical treatment for the patient, if needed, based on the step of measuring the condition of the patient.

47. The method of claim 46, wherein the step of measuring the patient's heart further comprising the steps of:

generating a set of parameters from the filtered blood pressure signal, each one of the set of parameters providing a measure of a particular function of the heart cycle of the patient at a first point in time;

generating a second set of parameters from a second filtered blood pressure signal, each one of the second set of parameters providing a measure of a particular function of the heart cycle of the patient at a second point in time;

comparing the first set of parameters and the second set of parameters; and determining the relative differences between the first set of parameters generated at the first point in time and the second set of parameters generated at the second point in time.

* * * * *